Figure 1:
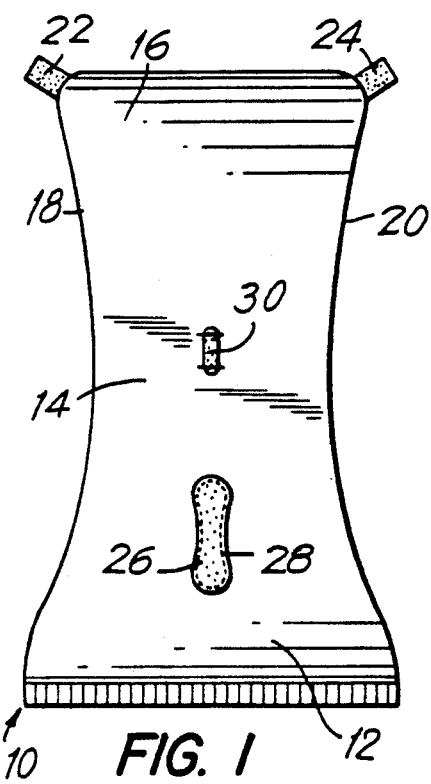

United States Patent [19]

Haque

[11] Patent Number: 5,037,413
[45] Date of Patent: Aug. 6, 1991

[54] DIAPER

[76] Inventor: Muhammad Haque, 113-04 Jewel Ave., Forest Hills, N.Y. 11375

[21] Appl. No.: 327,473

[22] Filed: Mar. 22, 1989

[51] Int. Cl.⁵ .............................................. A61F 13/16
[52] U.S. Cl. ............................... 604/385.1; 604/385.2
[58] Field of Search ................. 604/385.1, 385.2, 378, 604/369

[56] References Cited

U.S. PATENT DOCUMENTS

| | | | |
|---|---|---|---|
| 3,924,626 | 12/1975 | Lee et al. | 604/385.1 |
| 4,559,051 | 12/1985 | Hanson | 604/385.1 |
| 4,828,555 | 5/1989 | Hermansson | 604/385.1 |
| 4,895,568 | 1/1990 | Enloe | 604/385.1 |

Primary Examiner—Stephen C. Pellegrino
Assistant Examiner—Michael Rafa
Attorney, Agent, or Firm—Stanley J. Yavner

[57] ABSTRACT

A diaper is provided in forms to accommodate male and female wearers. In the male form, a pouch is provided in the area for accommodating the male genitalia, the pouch being formed with an absorbent pad. For the female wearer, an extra absorbent pad, but no pouch, is provided in the area for accommodating the female genitalia. In both forms, an absorbent pad is raised from the area of the diaper which accommodates the perineum of the wearer in order to prevent urine leaking back to the area of the anus of the wearer.

2 Claims, 1 Drawing Sheet

U.S. Patent     Aug. 6, 1991     5,037,413

DIAPER

This invention relates primarily to diaper constructions and more particularly to forming diapers with absorbent padding to provide maximum comfort and to prevent leaking of urine and flow of urine from the area of the genitalia to the area accommodating the anus of the wearer.

It is, of course, well-known that males and females are different. Likewise, baby males and baby females are also different, especially in terms of the genitalia. With present-day diaper construction, for the most part, there is little thought given to providing comfort, particularly for males, whose genitalia (scrotum and penis) extend from the body. Even if extra room is provided for the male, the formation of most diapers is with an absorbent capability throughout the entire area of the diaper. In this manner, leakage of urine and seeping of urine is more likely to occur for male wearers. As far as absorption is concerned in the area of the perineum, no thought by diaper designers seems to have been given to this device (perineum absorption) in terms of preventing flowing of urine back from the genitalia to the area of the anus.

Accordingly, a primary object of the present invention is to provide a comfortable and effective diaper construction.

A further and more particular object of the present invention is to provide a diaper construction, particularly for providing comfort to the male wearer.

A still further object of the present invention is to provide a diaper construction in forms for both male and female wearers whereby the male is accommodated both in terms of comfort and in terms of absorption and confinement of urine.

An additional object of the present invention is to provide for absorption and confinement of urine in the area of the diaper proximate the perineum of the wearer.

These and other objects of the present invention are provided in a diaper construction which includes a generally rectangular outline with a back portion, a central portion and a front portion. Of course, appropriate fasteners, well-known in the art, are provided to couple the furthest extent of the back portion to the furthest extent of the front portion, when the diaper is worn. Furthermore, the long sides of the rectangle are, as usual, slightly concave to accommodate the inside thigh portion of the wearer. The present invention features absorbent padding to prevent leaking or spreading of urine beyond the area of the genitalia of the wearer and for preventing flow of urine from the area of the genitalia to the area of the anus of the wearer. More particularly, for male wearers, a pouch is provided to accommodate the male genitalia, the pouch defining an absorbent pad to absorb urine. For a female wearer, an extra absorbent pad is provided in the area of the female genitalia, but without a pouch configuration because of the general lack of extension from the body in the area of the female genitalia. For both forms (male and female wearers) a padded ridge is provided in the area of the perineum, with absorbency in the ridge for preventing a flow of urine back from the genitalia to the anus.

Figure 2:
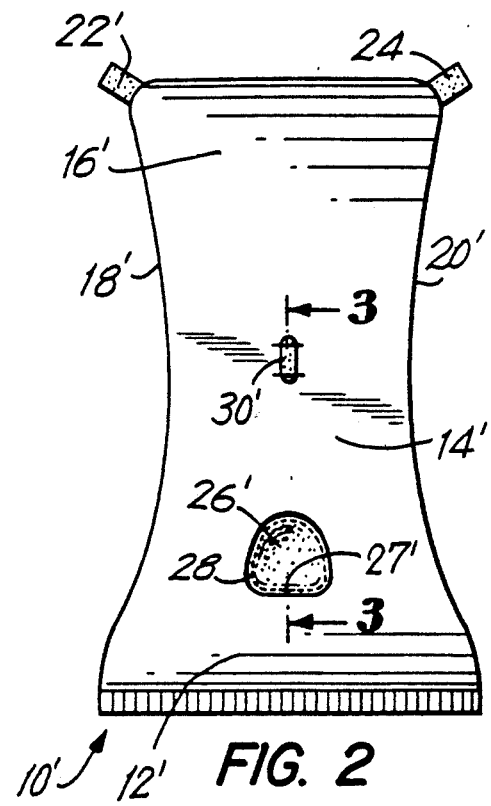
Figure 3:
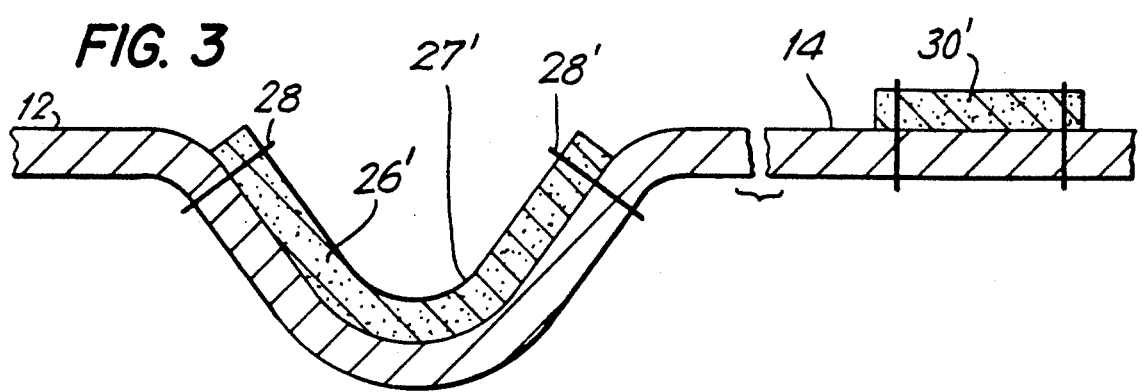

Other objects, features and advantages of the present invention will become apparent by the following detailed description of a preferred, but nonetheless illustrative embodiment of the present invention, with reference to the accompanying drawings, wherein FIG. 1 is a top plan view of a diaper according to the present invention, constructed particularly for female wearers;

FIG. 2 is a top plan view of a diaper according to the present invention, constructed particularly for male wearers; and FIG. 3 is a side sectional view, taken along the line 3—3 of FIG. 2, and showing particularly the pouch and perineum ridge construction, particularly suited for comfort and effectiveness with respect to male wearers.

Referring to the drawings, and particularly to FIG. 1 thereof, a diaper construction, generally designated 10 is shown in the usual, generally rectangular form and having a front portion 12, a central portion 14 and a back portion 16. The long sides of the rectangle, 18, 20, are, as per the usual form, slightly concave to accommodate the upper inside thigh of the female wearer. Adhesive or like tabs 22, 24 are used to attach the back portion 16 to front portion 12 when the diaper is worn, in the usual manner.

Back portion 16 is intended to accommodate the anus area of the female wearer, central portion 14 is intended to accommodate the perineum area of the female body and front portion 12 is for accommodating the genital area of the female wearer. A highly absorbent pad 26 is sewn by stitches 28, of the like into an area of front portion 12, just large enough to account for variations in female genitalia placement on the body, and yet small enough to confine absorption of urine strictly to the genitalia area of the female wearer. More importantly, for the female wearer, an absorbent ridge 30 is raised inwardly toward the female body in the perineum area in order to prevent flow of urine from the front portion 12 to the rear portion 16 of the diaper. More particularly, for the female wearer, and just as well for the male wearer, as will be described, absorbent padded ridge 30 keeps the urine away from the faeces, in order to prevent the mess that would normally be caused by the mixture of urine and faeces.

With reference to FIGS. 2 and 3, the male wearer is provided with a slightly different form of diaper 10', whereby the general outline of diaper 10' is the same as for a female wearer, with concave sides 18', 20', a front portion 12', a central portion 14' and a back portion 16'. Likewise, tabs 22' and 24' are provided for the male wearer However, absorbent pad 26' is defined by a pouch 27' formed in the plane of diaper 10' in a direction away from the wearer in order to accommodate the scrotum and penis of the male wearer. Absorbent pad 26' is fastened by stitches 28', or the like in a manner similar to the form of diaper of FIG. 1.

As with the female diaper of FIG. 1, male diaper 10' includes a padded ridge 30' in the area of the male perineum to prevent flow of urine to the back portion of the diaper.

In this manner, as described in the foregoing, a diaper construction is provided for comfort of the male wearer and control of urine flow and leakage for both the male and female wearer.

The foregoing description is provided as a preferred embodiment of the present invention and to illustrate the present invention, but limitations to the scope of the invention are only according to the following claims:

What is claimed is:

1. A diaper for a human wearer with a perineum body area, having a relatively planar surface in approximately the shape of a rectangle with a front portion, a central portion and a back portion comprising, in combination, an absorbent pad proximate the front portion and a raised absorbent pad extending longitudinally of said rectangle in the central portion covering said perineum area only, in order to prevent flow between the area of said front portion and the area of said back portion.

2. Thee invention according to claim 1, wherein the front portion of said diaper is for accommodating the genitalia of the wearer and the central portion for accommodating the perineum of the wearer and, for male wearers, said absorbent pad is defined by a pouch for accommodating all of the male genitalia.

* * * * *